US 7,619,073 B2

(12) United States Patent
Schumann et al.

(10) Patent No.: US 7,619,073 B2
(45) Date of Patent: Nov. 17, 2009

(54) METHOD FOR PURIFYING ERYTHROPOIETIN

(75) Inventors: Christof Schumann, Breitscheid-Erdbach (DE); Michael Mack, Bad Vilbel (DE); Jan-Ole Hesse, Bad Nauheim (DE)

(73) Assignee: Bioceuticals Arzneimittel AG, Bad Vilbel (DE)

( * ) Notice: Subject to any disclaimer, the term of this patent is extended or adjusted under 35 U.S.C. 154(b) by 0 days.

(21) Appl. No.: 11/570,224

(22) PCT Filed: Jun. 7, 2005

(86) PCT No.: PCT/EP2005/006099

§ 371 (c)(1),
(2), (4) Date: Jun. 29, 2007

(87) PCT Pub. No.: WO2005/121173

PCT Pub. Date: Dec. 22, 2005

(65) Prior Publication Data

US 2007/0293420 A1    Dec. 20, 2007

(30) Foreign Application Priority Data

Jun. 8, 2004    (DE)    ........................ 10 2004 027 816

(51) Int. Cl.
*C07K 1/00*    (2006.01)
(52) U.S. Cl. ..................................... 530/412
(58) Field of Classification Search ....................... None
See application file for complete search history.

(56) References Cited

U.S. PATENT DOCUMENTS

| 5,744,587 | A | 4/1998 | Alaska et al. |
| 6,399,333 | B1 * | 6/2002 | Burg et al. .................. 435/69.6 |

| 2002/0146771 | A1 | 10/2002 | Burg et al. |

FOREIGN PATENT DOCUMENTS

| EP | 0 267 678 A1 | 9/1987 |
| EP | 0 228 452 B1 | 3/1995 |
| EP | 1428878 A1 | 6/2004 |
| WO | WO 96/35718 A1 | 11/1996 |
| WO | WO 99/28346 A1 | 6/1999 |
| WO | WO 00/27869 | * 5/2000 |
| WO | WO 03/045996 | 6/2003 |
| WO | WO 03/080852 A1 | 10/2003 |

OTHER PUBLICATIONS

European Pharmacopoeia, 4th Ed, (2002) p. 1123-28 (Jan. 2002:1316).*
Gokana A et al. "Chromatographic separation of recombinant human erythropoietin isoforms" Journal of Chromatography A. Elsevier, Amsterdam, NL, vol. 791, Nos. 1-2, Dec. 12, 1997.
International Preliminary Report on Patentability for PCT/EP2005/006099, Dec. 8, 2006.

* cited by examiner

*Primary Examiner*—Sheridan Swope
(74) *Attorney, Agent, or Firm*—Knobbe Martens Olson & Bear, LLP

(57) ABSTRACT

The invention relates to a method for producing recombined erythropoietin having a particularly high degree of purity (≧98%). The method consists of at least 5 chromatographic purification steps, i.e. at least two anion exchange chromatographs, at least one hydrophobic interaction chromatography, at least one affinity chromatography and at least one hydroxyapatite chromatography. In preferred embodiments, the method does not require any exclusion chromatography and any reversed-phase chromatography. The invention relates to, in particular, a method wherein the following chromatographic purification steps have the following order; i) a first anion exchange chromatography, ii) an affinity chromatography, which relates, preferably, to a dye affinity chromatography, iii) a hydrophobic interaction chromatography, iv) an hydroxyapatite chromatography and v) a second anion exchange chromatography.

16 Claims, No Drawings

METHOD FOR PURIFYING ERYTHROPOIETIN

CROSS REFERENCE TO RELATED APPLICATIONS

This application is a U.S. National Phase of PCT International Application Number PCT/EP2005/006099, filed on Jun. 7, 2005, designating the United States of America, which claims priority to German Application Number 10 2004 027 816.4 filed on Jun. 8, 2004. The disclosures of the above-described applications are hereby incorporated by reference in their entirety.

The present invention relates to a method for producing recombinant erythropoietin having a particularly high purity level (≧98%). The method comprises at least 5 chromatographic purification steps, viz at least two anion exchange chromatographies, at least one hydrophobic interaction chromatography, at least one affinity chromatography, and at least one hydroxy-apatite chromatography. In preferred embodiments, the method does not require any kind of exclusion chromatography and any kind of reversed-phase chromatography. In particular, the present invention relates to a method comprising the following chromatographic purification steps in the given order: i) a first anion exchange chromatography, ii) an affinity chromatography, which preferably is a dye affinity chromatography, iii) a hydrophobic interaction chromatography, iv) a hydroxyapatite chromatography, and v) a second anion exchange chromatography.

Erythropoietin, shortly referred to as EPO, is a glycoprotein stimulating the production of erythrocytes in the bone marrow. EPO is mainly produced in the kidneys and from there it arrives at its destination via the blood circulation. In case of renal failure, the damaged kidneys do not produce enough EPO or none at all, which causes that too less erythrocytes emerge from the stem cells of the bone marrow. This renal anemia can be treated by means of administering EPO in physiological quantities, which stimulate the production of erythrocytes in the bone marrow. The EPO used for administration can be obtained either from human urine or by means of genetic engineering methods. As EPO is present in the human body only in trace amounts, it is virtually impossible to isolate EPO from its natural source for therapeutic applications. Therefore, gene technological methods offer the only economical possibility of producing said substance in larger quantities.

Recombinant production of erythropoietin is possible since the human erythropoietin gene was identified in 1984. Since the early 90s, various drugs containing human erythropoietin, which was produced by genetic engineering in eukaryotic cells, in particular in CHO (Chinese Hamster Ovary) cells, have been developed. The production of recombinant human erythropoietin is, for example, described in EP-A-0 148 605 and EP-A-205 564.

Conventionally, recombinant production of erythropoietin is performed in CHO host cells. While the latter were formerly cultivated in culture medium, to which fetal bovine serum and sometimes also bovine insulin was added, nowadays cultivation is regularly performed in serum- and protein-free medium. In this manner, the risk of contaminations with bovine proteins, bovine viruses, bovine DNA, or other undesirable substances originating from the formerly employed additives, will already be reduced by cultivation itself. Serum- and protein-free media suitable for cultivating eukaryotic cells are available from various suppliers, for example the medium MAM-PF2, sold by, inter alia, Biocon-cept, Allschwil, Switzerland, or the media DMEM and DMEM/F12, offered, for example, by Invitrogen/Gibco, Eggenstein, Germany.

Also, various chromatographic purification methods for erythropoietin have already been described in the prior art. EP-A-0 228 452 describes a method for purifying biologically active erythropoietin from a liquid comprising the chromatographic steps of anion exchange chromatography and reversed-phase chromatography.

In EP-A-0 267 678, the purification of an erythropoietin produced in serum-free culture is described, wherein a dialysis, an ion exchange chromatography, a preparative reversed-phase HPLC, and a gel filtration chromatography are performed consecutively. Herein, the step of gel filtration chromatography can be replaced by an ion exchange chromatography. Likewise, it has been suggested to perform a dye affinity chromatography on a Blue Trisacryl column prior to the (first) ion exchange chromatography.

In EP-A-0 830 376, a method for purifying erythropoietin is described, wherein EPO from the culture supernatant is subjected to a dye affinity chromatography in the first step of the chromatographic purification. There follows, in the second step, a chromatography on a hydrophobized carrier, followed by a hydroxyapatite chromatography. Subsequent to this, a reversed-phase HPLC is conducted, followed by an anion exchange chromatography as the final chromatographic step.

EP-A-1 127 063 describes a method for purifying erythropoietin comprising the following steps: differential precipitation, hydrophobic interaction chromatography, diafiltration, anion exchange chromatography, cation exchange chromatography, and size exclusion chromatography. The individual purification steps are conducted in the order mentioned in EP-A-1 127 063. In a variant of the method, the purification comprises the following steps: differential precipitation, hydrophobic interaction chromatography, diafiltration, anion exchange chromatography, cation exchange chromatography, a further diafiltration, and size exclusion chromatography. In any case, the method provides for a precipitation in the first step, followed by a centrifugation. Likewise, a gel filtration as the final step of the chromatographic purification is mandatory.

The international application WO-A-03/045996 describes a method for purifying EPO comprising an anion exchange chromatography, followed by a reversed-phase chromatography and a further anion exchange chromatography. The second anion exchange chromatography is followed by a size exclusion chromatography using a gel filtration medium.

The purification of erythropoietin is also an object of EP-A-0 428 267. Herein, a chromatographic step is performed on a Q Sepharose column, partially followed by reversed-phase chromatography and gel filtration.

It is a problem of the present invention to present a method for purifying erythropoietin, which preferably does without cost-intensive chromatographic steps as well as extensive steps, which may in addition require the use of undesirable reagents. The erythropoietin obtained by the purification method according to the present invention is supposed to meet the criteria for purity, which are set forth by the admission authorities or in the European Pharmacopoeia. In particular, the content of proteins originating from the host cell (host cell protein) is supposed to be below 100 ppm. Likewise, the content of DNA from the host cell is supposed to be lower than 100 pg/mg erythropoietin. Finally, with respect to its isoforms composition, the erythropoietin obtained by purification is supposed to be in accordance with the standard defined in the European Pharmacopoeia, 4th Ed, (2002) pp. 1123-28 (01/2002:1316).

Likewise, the method should preferably manage without a reversed-phase chromatography, like for example an RP-HPLC. In this type of chromatography, reagents like acetonitrile are conventionally employed, which are difficult to remove from the protein afterwards and which can be harmful to humans. It is another disadvantage of the RP-HPLC, that often cost-intensive organic solvents are employed, which increase the expenses for purification. Moreover, organic solvents are questionable with respect to environmental damages and are difficult and dangerous to handle. Altogether, the means employed in reversed-phase chromatography are often undesirable.

It is apparent that, with respect to purity and glycosylation pattern, high demands are made on the erythropoietin product obtained from the purification. These high standards can only be met by means of a purification method, which is specialized for erythropoietin and which is the result of extensive studies and analyses.

These and further problems underlying the present invention are solved by means of the purification method according to claim 1. Preferred embodiments are described in the dependent patent claims.

Thus, the present invention relates to a method for the purification of erythropoietin from a solution, in particular from a culture supernatant, wherein the following steps a) to c) are performed in the given order: in step a) a first anion exchange chromatography, in step b) an affinity chromatography, a hydrophobic interaction chromatography, and a hydroxyapatite chromatography, wherein the order of the chromatographic purification steps within step b) is arbitrary, and in step c) a second anion exchange chromatography.

The purification method according to the present invention thus utilizes at least four different chromatographic separation methods, i.e. (i) the method of ion exchange on the basis of competitive interaction of charged ions, (ii) the method of hydrophobic interaction, which is characterized in that the non-polar surface regions of a protein adsorb to the weakly hydro-phobic ligands of a stationary phase in the presence of high salt concentrations, (iii) the method of affinity based on the specific and reversible adsorption of a molecule to an individual matrix-bound binding partner, and (iv) the method of hydroxyapatite chromatography based on the use of inorganic hydroxyapatite crystals.

These chromatographic principles mentioned are also correspondingly differentiated among experts (see, for example, Bioanalytik, F. Lottspeich, H. Zorbas (ed.), Heidelberg, Berlin, Germany, Spekltrum Akad. Verlag 1998). However, it should be emphasized that the mandatory affinity chromatography in step b) is not a hydroxyapatite chromatography. Rather, step b) comprises both an affinity chromatography and a hydroxyapatite chromatography.

In a preferred embodiment, the EPO purification method comprises, in the given order, a first anion exchange chromatography, an affinity chromatography, a hydrophobic interaction chromatography, a hydroxyapatite chromatography, and a second anion exchange chromatography.

Preferably, the affinity chromatography is a dye affinity chromatography.

In a preferred embodiment, the second anion exchange chromatography is conducted by means of performing an acidic washing step, wherein the alkaline isoforms of the erythro-poietin are eluted by significant reduction of the pH value and are thus separated from the final product. Herein, "acidic washing step" is understood to denote that the pH value of the washing buffer lies clearly within the acidic range, preferably between 2.0 and 5.5, particularly preferably between 3.0 and 4.5, and most preferably at about 4.0. A sodium acetate buffer is a particularly suitable buffer. Thus, said chromatographic step is particularly important with respect to the glycosylation pattern of the final EPO product.

The cultivation of the erythropoietin-producing host cells is done in a culture medium, which is free of proteins and animal components.

In preferred embodiments, no reversed-phase chromatography takes place at any stage of the EPO purification. Preferably, a gel filtration is also avoided.

It has been found that the erythropoietin obtained by the method according to the present invention has a host cell protein content of <100 ppm and a host cell DNA content of <100 pg/mg. In particular, the insufficient depletion of host cell protein is a common problem in purification methods of the prior art. Here, the method of the present invention offers particular advantages, as a reliable depletion down to below 100 ppm is achieved.

The erythropoietin obtained by the method according to the present invention has a purity of at least 95%, preferably of at least 98%, and particularly preferably of at least 99%, wherein the purity is determined by analytical RP-HPLC. However, the RP-HPLC conducted to this end serves for analytical purposes only; within the scope of the purification, it is preferred to omit an RP-HPLC.

The activity of the protein should be at least 100,000 IU/mg, preferably at least 110,000 IU/mg, and particularly preferably at least 120,000 IU/mg (see also, European Pharmacopoeia, 4th Ed, (2002) pp. 1123-28 (01/2002:1316).

The present invention also relates to pharmaceutical preparations containing the erythro-poietin purified according to the present invention. Usually, EPO is formulated in liquid form and as such is injected intravenously or subcutaneously. Suitable adjuvants in liquid formulations of EPO are, for example, buffers, like for example phosphate buffers, salts, like for example sodium chloride, stabilizers for EPO, like for example amino acids, sugars and sugar alcohols, as well as tensides, like for example polysorbate 20/80. Examples for formulations are described in EP-A-0 306 824, EP-A-0 607 156, and EP-A-0 909 564, see also the commercial products NeoRecormon®, Erypo® in the German "ROTE LISTE 2004".

Preferably, the erythropoietin purified according to the present invention is recombinant human erythropoietin, produced in eukaryotic cells. Preferably, the recombinant erythro-poictin is produced in mammalian cells, particularly preferably in CHO cells such as is described in EP-A-0 205 564 and EP-A-0 148 605. According to conventional protocols fermentation is conducted in commercially available culture media.

Within the scope of the present invention, "erythropoietin" is understood to denote any protein that is capable of stimulating erythrocyte formation in the bone marrow and can, according to the assay described in the European Pharmacopoeia, 4th Ed, (2002) pp. 1123-28(01/2002:1316), unambiguously be identified as erythropoietin (Determining the activity in polycythemic or normocythemic mice). The erythropoietin can be the wild-type human erythropoietin or a variant thereof having one or more amino acid substitutions, deletions, or additions. Likewise, the erythropoietin contained in the formulation according to the present invention can be a conjugate, in which the protein is present, for example, in conjugated form with polymers, like for example polyalkylene glycol, so-called PEGylated erythropoietin.

In the sense of the present invention, "purification of erythropoietin" or "enrichment of erythropoietin" is understood to denote that the protein erythropoietin is obtained from a mixture in very pure form, i.e. the erythropoietin contained in the mixture is enriched until there are substantially no proteins present other than erythropoietin.

The person skilled in the art is familiar with the chromatographic principles utilized in the method according to the present invention; in any case, they are described in detail in current manuals or protocols of the suppliers of chromatographic matrices. Suitable matrices and background information as well as instructions for performing the different chromatographies can be found, for example, in the product catalog and the product information of Amersham Biosciences (see also www dot amershambiosciences dot com), or also in the product catalog of Bio-Rad (see also www dot bio-rad dot com).

The anion exchange chromatographies can be conducted by conventional, commercially available anion exchanger resins or membranes. Typical anion exchanger resins, which can be employed, comprise functional groups like diethylaminoethyl (DEAE), which are for example: DEAE SEPHAROSE (Amersham Biosciences), MACRO-PREP DEAE (Bio-Rad), FRACTORGEL EMD DEAE (Merck); quaternary aminoethyl (QAE), for example: Toyopearl QAE (TOYO BIOSEP); quaternary ammonium, for example: Q SEPHAROSE XL (Amersham Biosciences), Q SEPHAROSE FF (Amersham Biosciences), Resource Q (Amersham Biosciences), SOURCE 30Q (Amersham Biosciences), MACRO-PREP High Q (Bio-Rad), TOYOPEARL Super Q (Toyo Biosep); dimethylaminoethyl (DMAE), for example: FRACTOGEL EMD DMAE (Merck); trimethylaminoethyl (TMAE), for example: FRACTOGEL EMD TMAE (Merck); SARTOBIND membrane adsorber (MA) Q100 (Sartorius).

Preferred anion exchangers are resins with quaternary or tertiary ammonium ligands. Thus, in a preferred embodiment of the method according to the present invention, for example each of Q SEPHAROSE XL (an anion exchanger resin comprising a quarternary ammonium functional group) or Source 30 Q (both available from Amersham Biosciences), are employed in the first and the second anion exchange chromatography. Particularly preferably, Q SEPHAROSE XL is used in the first anion exchange chromatography and SOURCE 30Q is used in the second anion exchange chromatography.

The affinity chromatography can also be conducted by conventional commercially available resins. By way of example, there are to be mentioned: Dye SEPHAROSE, Heparin SEPHAROSE, HITRAP Blue HP columns (Cibacron Blue F3G-A), Blue SEPHAROSE (Cibacron Blue F3G-A), peptide/ligand affinity resins, antibody affinity resins, lectin affinity resins, affinity chromatography on immobilized DNA or on immobilized nucleotides and on group-specific adsorption agents, like for example on agarose-coupled gelatin.

Preferably, said affinity chromatography is a dye affinity chromatography, in particular using Blue SEPHAROSE (for example Blue SEPHAROSE 6 Fast Flow by Amersham Biosciences). However, other dye affinity matrices are also suitable, like for example the product DYEMATREX by Millipore.

The hydrophobic interaction chromatography can also be conducted by means of conventional matrices. Suitable matrices are e.g. butyl, phenyl, propyl, or octyl SEPHAROSE (Amersham Biosciences), MACRO-PREP methyl or t-butyl (Bio-Rad), and FRACTOGEL EMD containing propyl or phenyl ligands (Merck). Preferably, the matrix is butyl SEPHAROSE (for example Butyl SEPHAROSE 4 Fast Flow by Amersham Biosciences).

For hydroxyapatite chromatography, conventional hydroxyapatite materials can be used. Hydroxyapatite is a form of calcium phosphate. Preferably, CHT ceramic hydroxyapatite (Bio-Rad) is employed; particularly preferably CHT ceramic hydroxyapatite type I (Bio-Rad) is used.

The isoforms pattern of the final EPO product, i.e. obtained by means of the method according to the present invention and determined subsequent to the second anion exchange chromatography, is comparable to the BRP-EPO standard (see European Pharmacopoeia, 4th Ed, (2002) pp. 1123-28 (01/2002:1316).

Without being restrictive, the following Examples are intended to illustrate the present invention.

EXAMPLES

EPO is produced in CHO cells. Fermentation is done according to standard protocols, as described for eukaryotic cells, in particular for CHO cells, in patent and scientific literature. Cultivation is performed in a culture medium, which is protein-free and free of animal components (for example MAM-PF2, available from Bioconcept Allschwil, Switzerland, according to the supplier's recommendations). Harvest is performed subsequently to a production phase lasting at most seven days. Herein, the cells are separated by means of a depth filter and subsequent 0.2 μm filtration. Alternatively, the cells can be removed by centrifugation. The cell-free filtrate is then concentrated by about the factor 10 by means of ultrafiltration and is diafiltrated against phosphate buffers. The diafiltration serves for reducing the conductivity to below 5 mS/cm in order to prepare the protein solution for the first chromatographic step, the so-called capture step.

Survey Purification Methods

1. Chromatographic Step (Capture, IEX 1)

As "capture" step, an ion exchange chromatography (IEX) on Q SEPHAROSE XL is conducted. In this first purification step, the agent erythropoietin is concentrated. Furthermore, said step serves for converting the agent into a more stable storage form.

Washing is conducted using 20 mM Na-phosphate, pH 7.5, and elution with 0.3 M sodium chloride at pH 7.5. Subsequently to the anion exchange chromatography, a 0.2 μm filtration can be performed.

2. Chromatographic Step (Affinity)

In the next step, an affinity chromatography on Blue SEPHAROSE 6 FF (from Amersham Biosciences) is conducted. After changing the buffer system on the column and after an additional washing step, elution is performed in 1 M sodium chloride. The eluate is mixed with saline buffer and isopropanol for the subsequent hydrophobic interaction chromatography.

3. Chromatographic Step (HIC)

In the next step, the eluate mixed with saline buffer and isopropanol is loaded onto a hydrophobic interaction chromatography column (HIC; Butyl SEPHAROSE 4 FF, by Amersham Biosciences). After a washing step (2 M sodium chloride in 10% isopropanol), elution of the agent is conducted with 0.75 M sodium chloride in 23% isopropanol (v/v).

4. Chromatographic Step (Hydroxyapatite)

The eluate from the hydrophobic interaction chromatography is then subjected to a hydroxyapatite chromatography (CHT-I Ceramic Hydroxyapatite, by Bio-Rad). It can be diluted beforehand. Preferably, dilution is performed by bringing the eluate of the HIC column directly in Tris buffer (20 mM Tris/HCl, 5 mM $CaCl_2$, pH 6.9). After dilution, the final isopropanol concentration preferably is about 9%. Said solution is then directly loaded onto the hydroxyapatite column.

After washing with 10 mM potassium phosphate buffer, the elution of the erythropoietin is performed. The pH value of the eluate is adjusted to pH 7.4 using HCl.

5. Chromatographic Step (IEX 2)

For the following and preferably final chromatographic step, the EPO-containing solution is loaded onto an ion exchanger matrix (SOURCE 30Q, by Amersham Biosciences). Said chromatographic step includes an acidic washing step with sodium acetate (pH 4.0) in order to deplete alkaline isoforms of the pharmaceutical agent. After adjustment of the pH value to pH 7.4 by an additional washing step, the elution of erythropoietin is conducted with 200 mM sodium chloride.

Subsequently, a 0.2 µm filtration can again be performed within the scope of the virus filtration. The agent solution is referred to as bulk and can be lyophilized by means of liquid nitrogen and can then be stored at –80° C.

The erythropoietin obtained can be formulated in form of a liquid formulation together with conventional pharmaceutically acceptable adjuvants.

The Individual Chromatographic Steps in Detail

1. First Anion Exchange Chromatography (Capture Step)

The equilibration of the Q SEPHAROSE XL matrix (0.6 L±0.05 L) is performed with 20 mM sodium phosphate, pH 7.5 (until the pH value is 7.5±0.3 and the conductivity is <5 mS/cm behind the column). Then, the samples are loaded. Subsequently, the column is washed with the equilibration buffer, i.e. 20 mM sodium phosphate, pH 7.5. For the subsequent elution, 20 mM sodium phosphate, 300 mM NaCl, pH 7.5, are used.

Within the scope of the capture step, an acidic washing step is usually omitted.

The purity of the eluted erythropoietin is >65%, determined by RP-HPLC.

Subsequently to the capture step, a 0.2 µm filtration can be conducted. Preferably, the eluate is pumped directly through a 0.2 µm filter during elution with sodium chloride.

2. Blue SEPHAROSE Affinity Chromatography

The equilibration of the column is conducted with 20 mM sodium phosphate, 0.1 M NaCl, pH 7.5. Subsequently, the sample obtained from the capture step is applied onto the column, wherein the sample can be diluted with 20 mM sodium phosphate, pH 7.5, beforehand in preparation for the affinity chromatography.

Then, a washing step is conducted with 20 mM Tris/HCl, 0.1 M NaCl, pH 7.5. The second washing step is performed with 20 mM Tris/HCl, 5 mM $CaCl_2$, 0.1 M NaCl, pH 7.5. The elution is conducted with 100 mM Tris/HCl, 5 mM $CaCl_2$, 1 M NaCl, pH 7.5.

The Blue SEPHAROSE affinity chromatography serves, inter alia, for depleting host cell protein. Usually, the content of host cell protein is determined via ELISA. These and other strategies for analyzing host cell protein content can be looked up, for example, in Hoffman K. (2000) Biopharm, Vol. 13, No. 6, pp 38-45.

The yield of erythropoietin, measured by means of RP-HPLC, after Blue SEPHAROSE affinity chromatography is at least 65%, preferably at least 70%. The purity, also measured by means of RP-HPLC, is at least 90%, preferably at least 95%.

3. Hydrophobic Interaction Chromatography (HIC)

The hydrophobic interaction chromatography is conducted with Butyl SEPHAROSE 4 FF as matrix. Said matrix is physically stable and allows high flow rates.

The salt concentration (2 M NaCl) required for binding EPO is adjusted by means of mixing the eluate of the Blue SEPHAROSE 6 FF with 4 M NaCl buffer. In addition, the sample is adjusted to 10% isopropanol (v/v).

If possible, the conductivity of the sample provided for loading the HIC column should lie between 95 and 110 mS/cm. The conductivity of the equilibration buffer should also lie within said range.

The HIC column is equilibrated with 20 mM Tris/HCl, 2 M NaCl, 10% isopropanol, pH 7.5. Subsequent to sample load, washing with the equilibration buffer is conducted. The elution is performed with the following elution buffer: 20 mM Tris/TiC, 5 mM $CaCl_2$, 0.75 M NaCl, 23% (v/v) isopropanol, pH 6.9. The elution volume is 1 column volume.

It has shown that, within the scope of the purification method illustrated in detail herein, an isopropanol concentration of 23% (v/v) in the elution buffer leads to an optimal EPO elution, while simultaneously losses are minimized.

In order to avoid precipitation of the EPO by long-term reaction of isopropanol (23%, v/v), the eluate is brought directly into Tris buffer during the elution. Finally, the isopropanol concentration of the diluted eluate is 9% (v/v).

The yield of erythropoietin after this chromatographic step is at least 65%, preferably at least 70%, particularly preferably at least 80%. The purity is at least 92%, preferably at least 95%.

4. Hydroxyapatite Chromatography

The eluate of the Butyl SEPHAROSE 4 FF chromatography can be loaded onto the hydroxyapatite column (HAP) without further conditioning. Thereby, for the equilibration of the column, an isopropanol-containing Tris equilibration buffer results from the elution conditions of the hydrophobic interaction chromatography. Subsequent to loading the column, the isopropanol is removed by means of a washing step.

The buffers employed for the hydroxyapatite chromatographic step are as follows: Equilibration buffer: 20 mM Tris/HCl, 5 mM $CaCl_2$, 0.25 M NaCl, 9% isopropanol, pH 6.9.

The first washing step is conducted with the equilibration buffer, the second washing step with: 10 mM Tris/HCl, 5 mM $CaCl_2$, pH 6.8. The elution buffer is as follows: 10 mM Tris/HCl, 0.5 mM $CaCl_2$, 10 mM $K_2HPO_4$, pH 6.8.

The yield of the hydroxyapatite chromatographic step is at least 65%, preferably at least 70%. The purity of the EPO obtained is at least 97%, preferably at least 98%.

Altogether, the chromatography by means of hydroxyapatite serves for removing the isopropanol from the hydrophobic interaction chromatographic step. The elution of the EPO from the hydroxyapatite column can preferably be conducted by a gradient elution (from 0 to 10 mM potassium phosphate). However, a linear gradient (for example from 0 to 40 mM potassium phosphate) can also be employed.

In a preferred embodiment of the method according to the present invention, a virus filtration is performed after the hydroxyapatite chromatography. Said virus filtration can be conducted, for example, with a PLANOVA 15N filter by the Asahi Kasei Group. The filter membrane has a pore size of 15 nm and also ensures the depletion of polioviruses and parvoviruses.

5. Second Ion Exchange Chromatography

As the final purification step, an ion exchange chromatography by means of SOURCE 30Q is performed. In particular, said step is characterized by an acidic washing step, by which the alkaline isoforms of the erythropoietin are eluted by a drop in the pH value and are thus separated from the final product. Said chromatographic step is thus of particular importance with respect to the glycosylation pattern of the final EPO product.

A phosphate buffer is used as buffer system for the second ion exchange step for purifying erythropoietin. After loading the sample and subsequently to the first washing step, an "acidic" washing step is conducted. Alkaline isoforms of the erythropoietin are eluted under these conditions.

The equilibration and the first washing step are conducted with 10 mM sodium phosphate, pH 7.4. The acidic washing step is conducted with a washing buffer having a sodium acetate content of 20 mM and a pH value of 4.0. The washing volume of the acidic washing step is 2 column volumes.

Subsequently, one more washing step with a phosphate buffer is usually performed, whereby the pH value is increased to 7.4. The elution is conducted with a cascade gradient from 0 to 0.2 M NaCl. However, a linear gradient, for example from 0 to 0.5 M NaCl, is also suitable.

The elution buffer has the following composition: 20 mM sodium phosphate, 0.2 M NaCl, pH 7.4. The elution is performed over 1.5 column volumes.

The yield is at least 65%, preferably at least 70%, and particularly preferably at least 75%. The purity is at least 98%, preferably at least 99%.

The EPO product finally obtained has a biological activity of $\geq$100,000 IU/mg in a bio-assay, a DNA content of <100 pg/mg protein, an EPO purity of $\geq$98%, a host cell content (HCP, host cell protein) of <100 ppm, and an isoforms pattern (in the CZE) fulfilling the requirements of the European Pharmacopoeia.

By the way, all column chromatographies are conducted according to the recommendations and protocols of the suppliers of the matrices or the columns (for example with respect to flow rates, column volumes employed for washing or for elution, diameters and bed heights of the columns, etc.).

The invention claimed is:

1. A method for enrichment of erythropoietin from a culture supernatant produced by culturing eukaryotic host cells in culture medium, comprising the following steps a)-c) carried out in the order given:

a) a first anion exchange chromatography;

b) an affinity chromatography, a hydrophobic interaction chromatography and a hydroxyapatite chromatography in the order given; and c) a second anion exchange chromatography comprising an acidic wash step.

2. The method of claim 1, wherein the affinity chromatography is a dye affinity chromatography.

3. The method of claim 1, further comprising at least one filtration step.

4. The method of claim 3, wherein the at least one filtration step is carried out after the last chromatographic purification step of step b).

5. The method of claim 3, wherein the at least one filtration is carried out after the second anion exchange chromatography.

6. The method of claim 1, wherein the protein mixture is a host cell-free filtrate of the culture medium, which is subjected to diafiltration prior to the first anion exchange chromatography.

7. The method of claim 6, wherein the host cell-free filtrate is subjected to ultrafiltration prior to the diafiltration.

8. The method of claim 1, wherein the culture medium is protein-free and animal component-free.

9. The method of claim 1, wherein the method does not comprise reverse phase chromatography.

10. The method of claim 1, wherein the method does not comprise gel filtration chromatography.

11. The method of claim 1, wherein the method does not comprise protein precipitation.

12. The method of claim 1, wherein the method does not comprise any further chromatographic purification steps.

13. The method of claim 1, wherein the enriched erythropoietin, after the second anion exchange chromatography, has a host cell protein content of less than 100 ppm.

14. The method of claim 1, wherein the enriched erythropoietin, after the second anion exchange chromatography, has a host cell DNA content of less than 100 pg/mg.

15. The method of claim 1, wherein the enriched erythropoietin, after the second anion exchange chromatography, has a purity of at least 98%, determined by RP-HPLC.

16. The method of claim 1, wherein the enriched erythropoietin, after the second anion exchange chromatography, has an activity of at least 100,000 IU/mg.

* * * * *